United States Patent [19]
Beasley et al.

[11] Patent Number: 5,912,252
[45] Date of Patent: Jun. 15, 1999

[54] PURINE AND GUANINE DERIVATIVES AS PNP INHIBITORS

[75] Inventors: Steven Colin Beasley; John Gary Montana, both of Cambridge, United Kingdom

[73] Assignee: Darwin Discovery Limited, United Kingdom

[21] Appl. No.: 08/849,438

[22] PCT Filed: Oct. 7, 1996

[86] PCT No.: PCT/GB96/02444

§ 371 Date: May 19, 1997

§ 102(e) Date: May 19, 1997

[87] PCT Pub. No.: WO97/12887

PCT Pub. Date: Apr. 10, 1997

[30] Foreign Application Priority Data

Oct. 5, 1995 [GB] United Kingdom ................... 9520364

[51] Int. Cl.⁶ .................... C07D 473/18; C07D 473/30; C07D 498/04; A61K 31/52

[52] U.S. Cl. ................ 514/262; 544/255; 544/276; 544/277; 544/319; 544/320; 544/321

[58] Field of Search ..................... 544/276, 277; 514/262

[56] References Cited

FOREIGN PATENT DOCUMENTS

| 156559 | 10/1985 | European Pat. Off. . |
| 178178 | 4/1986 | European Pat. Off. . |
| 91/06548 | 5/1991 | WIPO . |
| 90/11283 | 10/1991 | WIPO . |

OTHER PUBLICATIONS

Reily, Inorg. Chem 24, 37–43, 1985.
Montgomery, J. Med. Chem 15, 1189, 1972.
Otsuka, Chem Abs 77, 101650g, 1972.
Michael, J. Med Chem 36, 3431, 1993.
Baker, J. Med Chem. 10, 62–4 1967.
Schaeffer, J. Pharm. Sci 60, 1204 1971.

*Primary Examiner*—Mark Berch
*Attorney, Agent, or Firm*—Saliwanchik, Lloyd & Saliwanchik

[57] ABSTRACT

The subject invention concerns compounds of formula (I):

wherein
n=1 or 2;
$R^1$ is H, $NH_2$ or halogen;
$R^2$ is H or $NH_2$;
$R^3$ represents the group $CR^6R^7R^8$ where $R^6$, $R^7$ and $R^8$ are the same or different and are each H, $C_{1-6}$ alkyl or $C_{1-6}$ haloalkyl;
$R^4$ and $R^5$ are the same or different and are selected from the group consisting of H, $CO_2H$, $CO_2C_{1-6}$, $NHSO_2CF_3$, tetrazole and $(CR^9R^{10})_p(Y)_q(CR^9R^{10})_tZ$ where $(CR^9R^{10})_p$ or $(CR^9R^{10})_t$ is straight or branched chain bearing the substituents $R^9$ and $R^{10}$ when p or t>1;
$R^9$ and $R^{10}$ are the same or different and are each $C_{0-6}$ alkyl-Z;
p=1–3;
q=0 or 1;
t=0–4, provided that t>0 when q=1;
Y=O, NH or $S(O)_m$ where m=0–2; and
Z is selected from a group consisting of H, CN, $CO_2H$, $CO_2C_{1-6}$ alkyl, $NHSO_2CF_3$ tetrazole, triazole, $CONH_2$, $CON(C_{1-6}$ alkyl$)_2$, $CONH(C_{1-6}$ alkyl), SO, N H ($C_{1-6}$ alkyl) and $SO_2N(C_{1-6}$ alkyl$)_2$;
or a salt, solvate or hydrate thereof. The subject invention also pertains to methods of using the subject compounds.

7 Claims, No Drawings

PURINE AND GUANINE DERIVATIVES AS PNP INHIBITORS

This application is a 371 of PCT/GB96/02444, filed Oct. 7, 1996.

FIELD OF THE INVENTION

The invention relates to purine and guanine derivatives and their use purine nucleoside phosphorylase (PNP) inhibitors, for treating conditions in mammals which are responsive to purine nucleoside phosphorylase inhibition.

BACKGROUND OF THE INVENTION

9-Arylmethyl-substituted purines (including guanines) have been reported as PNP inhibitors in EP-A-0,178,178 substantially corresponding to U.S. Pat. No. 4,772,606. 9-arylmethyl-substituted purines (including guanines), in which the aryl ring contains phosphonic acid groups, have also been reported as PNP inhibitors in EP-A-0,465,297 WO-A-92/05180. Modified purines, namely 9-deazapurines, have also been reported as PNP inhibitors in U.S. Pat. No. 4,985,434; U.S. Pat. No. 5,008,265; U.S. Pat. No. 4,985,433; U.S. Pat. No. 5,236,926; U.S. Pat. No. 5,236,926 and U.S. Pat. No. 5,008,270.

PNP inhibitory data cited in Drugs of the Future, 13, 654 (1988), Agents and Actions, 21, 253 (1987), Proc Natl Acad Sci USA, 88, 11540 (1991) and U.S. 90/01021 indicate that modifications to the guanine base markedly alter the PNP inhibitory ability of such compounds. Also, modifications to the aryl ring of the 9-deaza (9-arylmethyl) purines can markedly alter PNP inhibitory activity. Namely replacement of a pyridine ring with piperidine greatly reduces activity as illustrated in IL Farmaco, 48 (2), 297 (1993).

SUMMARY OF THE INVENTION

The compounds of the invention are particularly useful in mammals as purine nucleoside phosphorylase (PNP) inhibitors, as selective inhibitors of T-cells and for suppressing cellular immunity. They can thus be used for the treatment of autoimmune diseases, transplant rejection, psoriasis or gout in mammals. They can also be used to potentiate the antiviral and antitumor effect of antiviral or antitumor purine nucleosides.

The present invention relates to the compounds of formula (I), their tautomers, salts, solvates and hydrates.

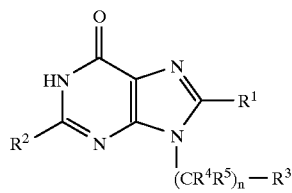

(I)

wherein
n=1,2;
$R^1$ represents H or the group $NH_2$ or halogen;
$R^2$ represents H or the group $NH_2$;
$R^3$ represents the group $CR^6R^7R^8$ where $R^6$, $R^7$ and $R^8$ may be the same of different, and may be H or the group $C_{1-6}$ alkyl or $C_{1-6}$ haloalkyl.
$R^4$ and $R^5$ may be the same or different and may be H or the group $CO_2H$, $CO_2C_{1-6}$ alkyl, $NHSO_2CF_3$ tetrazole or $(CR^9R^{10})p(Y)q(CR^9R^{10})tZ$ where the group $(CR^9R^{10})p$ or $(CR^9R^{10})t$ may be straight or branched chain bearing the substituents $R^9$ and $R^{10}$ when p or t>1.
$R^9$ and $R^{10}$ may be the same or different, and may be H or the group $C_{0-6}$ alkyl Z
p=1–3
q=0,1
t=0–4
Y=O, NH, $S(O)_m$ where m=0–2.
Z represents H or the group CN, $CO_2H$, $CO_2C_{1-6}$ alkyl, $NHSO_2CF$, tetrazole, triazole, $CONH_2$, $CON(C_{1-6}alkyl)_2$, $CONH(C_{1-6}alkyl)$, $SO_2$ N H ($C_{1-6}$ alkyl), $SO_2N(C_{1-6}$ alkyl$)_2$.

Combinations of substituents and/or variables are permissible only if such combinations result in stable compounds; thus t>0 when q=1.

DESCRIPTION OF THE INVENTION

It will be appreciated that the compounds according to the invention can contain one or more asymmetrically substituted carbon atoms. The presence of one or more of these asymmetric centres in a compound of formula (I) can give rise to stereoisomers, and in each case the invention is to be understood to extend to all such stereoisomers, including enantiomers and diastereomers, and mixtures including racemic mixtures thereof.

In the formulae herein, the ~ line is used at a potential asymmetric centre to represent the possibility of R- and S-configurations, and the < line and the . . . line to represent a unique configuration at an asymmetric centre.

As used in this specification, alone or in combination, the term "$C_{1-6}$ alkyl" refers to a straight or branched chain alkyl moiety having from one to six carbon atoms, including for example, methyl, ethyl, propyl, isopropyl, butyl, t-butyl, pentyl, hexyl and the like.

As used in this specification, alone in combination, the term "$C_{1-6}$ haloalkyl" refers to a straight or branched chain alkyl moiety having from one to six carbon atoms optionally substituted with one or more halogen atoms including for example trifluoromethyl, pentafluoroethyl, trifluorodichloroethyl and the like.

As used in this specification, alone or in combination, the term "$C_{0-6}$ alkyl" refers to a straight chain alkyl moiety having from zero to six carbon atoms, including for example methyl, ethyl, propyl etc.

The term "halogen" means fluorine, chlorine, bromine or iodine.

Salts of compounds of formula (I) include pharmaceutically acceptable salts, for example acid addition salts derived from inorganic or organic acids, such as hydrochlorides, hydrobromides, hydroiodides, p-toluenesulphonates, phosphates, sulphates, perchlorates, acetates, trifluoroacetates, propionates, citrates, malonates, succinates, lactates, oxalates, tartrates and benzoates.

Salts may also be formed with bases. Such salts include salts derived from inorganic or organic bases, for example alkali metal salts such as magnesium or calcium salts, and organic amine salts such as morpholine, piperidine, dimethylamine or diethylamine salts.

As part of the current invention, any group of compounds in which an ester function is present, that ester may take the form of a metabolically labile ester in which the alcohol portion constitutes, for example, an ethyl, benzyl, phenethyl, phenylpropyl, α or β-naphthyl, 2,4-dimethylphenyl, 4-tert-butylphenyl, 2,2,2-trifluoroethyl, 1-(benzyloxy)benzyl, 1-(benzyloxy)ethyl, 2-methyl-1-propionyloxypropyl, 2,4,6-trimethylbenzyloxymethyl or pivaloyloxymethyl group.

Also claimed as part of the invention are compounds that may be converted metabolically to any compound of formula (I) during therapeutic use of such compound. As a non-limiting example of this, compounds described by formula (I) where the 6-oxo (also known as the 6-hydroxy tautomer) substituent is absent and replaced by a hydrogen atom may be converted to compounds of general formula (I) by the action of known processes of metabolism, and thus comprise part of the current invention. Further examples are known to those skilled in the art.

It will also be recognised by those skilled in the art that guanines of formula (I) can exist in the tautomeric forms depicted below.

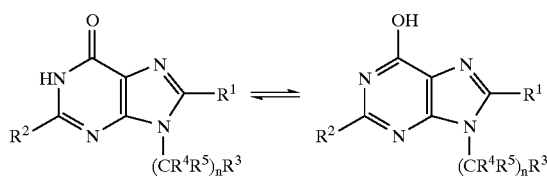

Particularly preferred compounds according to the invention include:

8-Amino-9-(3',3'-dimethylbutyl)guanine
8-Amino-9-(2'-methylpropyl)guanine
8-Amino-9-(3'-methylbutyl)guanine
and their salts, e.g. their dihydrochlorides.

The compounds of the invention are particularly useful for selectively suppressing T-cell mediated immunity in mammals without diminished effect on humoral (B-cell) immunity, and for treating or preventing conditions in mammals in which T-cells are involved, such as conditions associated with or mediated by T-cell proliferation, these include but are not restricted to resistance to transplantation or transplantation rejection of organs or tissues (such as heart, kidney, liver, lung, bone marrow, cornea, pancreas, intestinum tenue, limb, muscle, nervus, medulla ossium, duodenum, small-bowel, skin, pancreatic islet-cell, etc. including xeno transplantation), graft-versus-host diseases by medulla ossium transplantation, autoimmune diseases such as rheumatoid arthritis, systemic lupus erythematosis, nephrotic syndrome lupus, Hashimoto's thyroiditis, multiple myasthenia gravis, type I diabetes mellitus, type II adult onset diabetes, uveitis, nephrotic syndrome, steroid-dependent and steroid resistant nephrosis, Palmo-planter pustulosis, allergic encephalomyelitis, glomerulonephritis, etc., and infectious diseases caused by pathogenic microorganisms.

The compounds of formula (I) are also useful in the treatment of Gout, T-cell Leukaemia, T-cell cancers, Irritable bowel disease, Crohn's disease and Ulcerative colitis.

The compounds of formula (1) are also useful for treating inflammatory, proliferative and hyperproliferative skin diseases and cutaneous manifestations of immunologically-mediated illnesses such as: psoriasis, psoriatic arthritis, atopical dermatitis, contract dermatitis and further eczematous dermatitises, seborrhoeic dermatitis, Lichen planus, Pemphigus, bullous Pemphligoid, Epidermolysis bullosa, urticaria, angioedemas, vasculitides, erythemas, cutaneous eosinophilias, acne, Alopecia areata, eosinophilic fascitis, and atherosclerosis. More particularly, the compounds of formula (1) are useful in hair revitalising, such as in the treatment of male or female pattern alopecia or alopecia senilis, by providing epilation prevention, hair germination, and/or a promotion of hair growth.

The compounds of formula (1) are useful in the treatment of respiratory diseases, for example sarcoidosis, fibroid lung, idiopathic interstitial pneumonia, and reversible obstructive airways disease, including bronchial asthma, allergic asthma, intrinsic asthma, extrinsic asthma and dust asthma, particularly chronic or inveterate asthma (for example late asthma and airway hyper-responsiveness), bronchitis and the like. The compounds of formula (1) may also be useful for treating hepatic injury associated with ischaemia.

The compounds of the invention are also indicated in certain eye diseases such as keratoconjunctivitis, vernal conjunctivitis, uveitis associated with Behcet's disease, keratitis, herpetic keratitis, conical cornea, dystrophia epithelialis corneae, corneal leucoma, ocular pemphigus, Mooren's ulcer, Scleritis, Graves' ophthalmopathy, severe intraocular inflammation and the like.

The compounds of formula (1) are also useful for preventing or treating inflammation of mucosa or blood vessels (such as leukotreine $B_4$-mediated diseases, gastric ulcers, vascular damage caused by ischaemic diseases and thrombosis, ischaemic bowel disease, inflammatory enterocolitis), or intestinal lesions associated with thermal burns, cytomegalovirus infection, particularly HCMV infection.

Further, the compounds of formula (1) are also useful for treating or preventing renal diseases including interstitial nephritis, Goodpasture's syndrome, hemolytic-uraemic syndrome and diabetic nephropathy; nervous diseases selected from multiple myositis, Guillain-Barre syndrome, Meniere's disease and radiculopathy; endocrine diseases including hyperthyroidism and Basedow's disease; haematic diseases including pure red cell aplasia, aplastic, aplastic anaemia, hypoplastic anaemia, agranulocytosis; respiratory diseases including sarcoidosis, fibroid lung and idiopathic interstitial pneumonia; skin diseases including dermatomyositis, leukoderma vulgaris, ichthyosis vulgaris, photoallergic sensitivity and cutaneous T cell lymphoma; circulatory diseases including arteriosclerosis, aortitis syndrome, polyarteritis nodosa and myocardosis; collagen including scleroderma, Wegener's granuloma and Sjorgen's syndrome; adiposis; eosinophilic fascitis; periodontal disease; nephrotic syndrome; hemolytic-uraemic syndrome; and muscular dystrophy.

Further, the compounds of the invention are indicated in the treatment of diseases, including intestinal inflammation/allergies such as Coeliac disease, proctitis, eosinophilic gastroenteritis, mastocytosis, and food related allergic diseases which have symptomatic manifestation remove from the gastrointestinal tract, for example migraine, rhinitis and eczema.

The compounds of the invention also have liver regenerating activity and/or activity in stimulating hypertrophy and hyperplasia of hepatocytes. Therefore, they are useful for the treatment and prevention of hepatic diseases such as immunogenic diseases (e.g. chronic autoimmune liver diseases including autoimmune hepatitis, primary biliary cirrhosis and sclerosing cholangitis), partial liver section, acute liver necrosis (e.g. necrosis caused by toxins, viral hepatitis, shock or anoxia), B-virus hepatitis, non-A/non-B hepatitis and cirrhosis.

The compounds of the invention are also useful for inhibiting the in vivo metabolic degradation of purine nucleosides via phosphorolysis and are thus useful to potentiate the antiviral and antitumor efficacy of 2' and/or 3'-mono- or dideoxy purine nucleosides. For instance, they are useful for potentiating e.g. 2',3'-dideoxyadenosine, 2'3'-dideoxyguanosine or 2',3'-dideoxyinosine for the treatment of retrovirus infections such as acquired immunodeficiency syndrome (AIDS). They are also useful for potentiating the antitumor/cytotoxic effect of e.g. 2'-deoxyguanosine in mammals.

The compounds of the invention are also useful in coadministration with other immunosuppressive agents such as, but not limited to cyclosporin A for use in transplant rejection. Such combination prolongs graft survival to a greater extent than when a single drug therapy is used. therefore increased benefit arises from being able to lower the dose of the immunosuppressant so reducing the potential for drug related side effects, see Chung-Yang Yen et al J. Surgical Research. 62, 260 (1996).

The compounds of the invention are also useful for the treatment of parasitic disorders in which the parasite uses PNP to generate its own DNA constituents (ie the purine bases). Inhibition of the parasite PNP by compounds of the present invention in, for example malaria, causes death of the parasite.

The above-cited properties are demonstrable in in vitro and in vivo tests using advantageously mammals, e.g. rats, mice, dogs, calves, and isolated cells thereof. Said compounds can be applied in vitro in the form of solutions, e.g. preferably aqueous solutions and in vivo either enterally or parenterally, advantageously orally and intravenously. The dosage in vitro may range between about $10^{-4}$ and $10^{-10}$ molar concentrations. The dosage in vivo may range, depending on the route of administration, between about 0.001 and 300 mg/kg.

PNP inhibition is measured radiochemically by measuring the formation of $^{14}$C-ribose-1-phosphate from $^{14}$C-guanosine using a modification of the method employed previously (J. C. Sircar et al J. Med. Chem. 29, 1804 (1986)) employing calf spleen as the enzyme source and 1 mM phosphate. Results are expressed as $IC_{50}$ values, corresponding to the concentration of compound required to achieve a 50% reduction of the formation of ribose-1-phosphate.

The potentiation of the cell growth inhibitory activity (cytotoxicity) of 2'-deoxyguanosine (d-Guo) by the compounds of the invention is determined as follows: MOLT-4 cells are grown in RPMI-1640 medium. To suspension cultures of these cells, d-Guo at a fixed concentration of (10 mM) and the candidate PNP inhibitor at varied concentrations are added. The degree of cell proliferation is measured by addition of $^3$H-Thymidine for the final 16 hours of a total culture period of 72 hours. The level of incorporation of 3H-Thymidine is assessed by liquid scintillation spectrometry. From this data, the $IC_{50}$ is calculated as the concentration of PNP inhibitor required to reduce the incorporation of $^3$H-Thymidine to 50% of that of control cultures. This method is similar to that used previously to determine the effectiveness of PNP inhibitors on the potentiation of the toxicity of d-Guo (I. S. Kazmers, Science, 24, 1137–1139 (1981)).

Demonstration of the efficacy of compounds of formula I in an in vivo model of a T-cell mediated disease may be carried out by using the Dinitrofluorobenzene (DNFB) sensitised mouse model of contact dermatitis. DNFB is applied topically to young adult female Balb/c mice on days 1 and 2 in a suitable vehicle. On day 6 the animals may be challenged by application of DNFB to one ear. Compounds of the invention may be dosed by an appropriate route in an appropriate vehicle. Determination of efficacy may be carried out in a number of ways, an example of which is measurement of ear thickness using calipers. Results are expressed as percentage reduction in inflammatory response. This method is similar to that reported in WO94/23309.

Compounds of general formula (I) may be evaluated in an adjuvant arthritis model in the rat based on the methods employed by B. B. Newbould (1963), Br.J.Pharmacol, 21, 127–136 and C. M. Pearson and F. D. Wood (1959), Arthritis Rheum, 2, 440–459. Briefly male Wistar rats (180–200 g) are injected at the base of the tail with Freund's adjuvant. Twelve days later the responding animals are randomised into experimental groups. Compounds of general formula (I) are dosed either orally as a suspension in 1% methyl cellulose or intraperitoneally in 0.2% carboxymethylcellulose from day 12 to the end of the experiment on day 22. Hind paw volumes are measured every two days from day 12 onwards and X-rays taken of the hind feet on completion of the experiment. Results are expressed as the percent increase of foot volume over day 12 values.

PNP inhibition can also be determine in vivo essentially as described in Agents and Actions, 22, 379 (1987) by measuring compound induced increase in plasma inosine levels in the rat.

Compounds of the general formula (I) may be prepared by any suitable method known in the art and/or by the following processes, which itself forms part of the invention.

According to a second aspect of the invention, there is provided a process for preparing a compound of general formula (I) as defined above. It will be appreciated that where a particular stereoisomer of formula (I) is required, the synthetic processes described herein may be used with the appropriate homochrial starting material and/or isomers may be resolved from mixtures using conventional separation techniques (e.g. HPLC).

The compounds according to the invention may be prepared by the following processes. In the description and the formulae below the groups R1, R2, $R^3$, $R^4$, $R^5$, R6, R7, R8, $R^9$, R10 X, Y, Z, n, m, p, q, and t are as defined above, except where otherwise stated. It will be appreciated that functional groups, such as amino, hydroxyl or carboxyl groups, present in the various compounds described below, and which it is desired to retain, may need to be in a protected form before any reaction is initiated. In such instances, removal of the protecting group may be the final step in a particular reaction. Suitable protecting groups for such functionality will be apparent to those skilled in the art. For specific details see "Protective Groups in Organic Synthesis", Wiley Interscience, T. W. Greene, P. G. M. Wutts.

A process for preparing compounds of general formula (I) where $R^1$=NH$_2$ comprises deprotecting a compound of general formula (II)

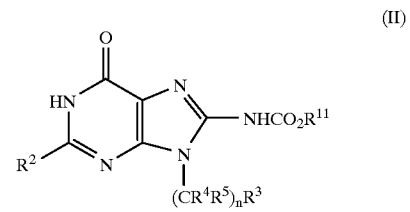

(II)

wherein $R^{11}$ represents a suitably labile group such as an alkyl group, e.g. ethyl, or an arylalkyl group, e.g. benzyl.

The deprotection reaction may be performed using standard conditions for hydrolysis reactions of this type. Thus, for example the reaction may be achieved in a solvent such as water containing an inert organic solvent such as an ether, e.g. a cyclic ether such as tetrahydrofuran, an amide, e.g. a substituted amide, such as dimethylformamide, or an alcohol, e.g. ethanol, in the presence of an inorganic base such as potassium carbonate or sodium hydroxide, at a temperature ranging from room temperature to the reflux temperature of the solvent mixture, preferably the reflux temperature of the solvent mixture.

Alternatively, when $R^{11}$ contains groups that are labile to hydrogenation, this may be performed as a method of deprotection. Thus, for example the reaction may be achieved in an inert solvent such as an alcohol, e.g. ethanol, in the presence of a transition metal catalyst, e.g. palladium on carbon, at a low temperature, preferably room temperature.

It will be appreciated that where a particular stereoisomer of formula (I) is required, this may be obtained by conventional resolution techniques such as high performance liquid chromatography. Where desired, however, appropriate homochiral starting materials may be used in the coupling reaction to yield a particular stereoisomer of formula (I). This is exemplified below.

Intermediates of general formula (II) may be prepared by rearrangement of intermediates of general structure (III)

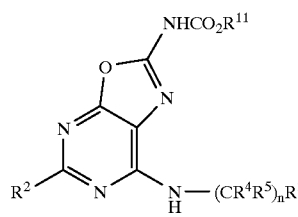

(III)

The rearrangement reaction may be performed using standard conditions for this reaction as outlined by J. Wang et al., J. Org. Chem., 53, 5617 (1988). Thus, the reaction may be achieved in a solvent, for example an inert organic solvent such as an ether, e.g. a cyclic ether such as tetrahydrofuran, an amide, e.g. a substituted amide such as dimethylformamnide, or an alcohol such as ethanol at a temperature ranging from ambient temperature to the reflux temperature of the solvent, preferably the reflux temperature of the solvent, in the presence of an inorganic base such as potassium carbonate or sodium methoxide.

Intermediates of general formula (III) may be prepared from thioureas of general formula (IV)

(IV)

This transformation may be performed using the procedure outlined by J. Wang et al., J. Org. Chem., 53, 5617 (1988). Thus, for example the reaction may be undertaken in the presence of an inert organic solvent such as an ether, e.g. a cyclic ether such as tetrahydrofuran, an amide e.g. a substituted amide such as dimethylformamide, or a nitrile such as acetonitrile, at ambient temperature, preferably 20–30° C., in the presence of a diimide, e.g. dicyclohexylcarbodiimide.

It is also an aspect of the present invention that intermediates of formula (II) may be prepared from intermediates of formula (IV) by combining the above documented procedures in one step.

Thioureas of general formula (IV) may be prepared from amines of general formula (V)

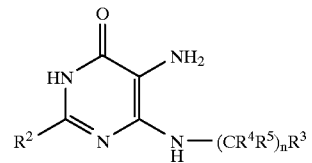

(V)

and isothiocyanates of general formula $S=C=NHCO_2R^{11}$ (VI).

This transformation may be performed using the procedure outlined by J. Wang et al., J. Org. Chem., 53, 5617 (1988). Thus, for example the reaction may be undertaken in the presence of an inert organic solvent such as an ether, e.g. a cyclic ether such as tetrahydrofuran, a nitrile such as acetonitrile or a halogenated hydrocarbon such as dichloromethane, at a low temperature, preferably ambient temperature, optionally in the presence of a base, e.g. an organic base such as an amine, e.g. triethylamine.

The isothiocyanates of general formula (VI) may be prepared by the general procedure of J. Wang et al., J. Org. Chem., 53, 5617 (1988).

The amines of general formula (V) may be prepared by reduction of nitro derivatives of general formula (VII)

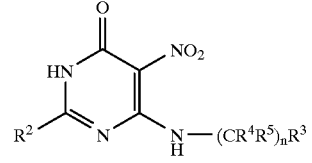

(VII)

It will be appreciated by those skilled in the art, that reduction reactions of this type can be affected by several methods as outlined in Advanced Organic Chemistry (4th edition), J. March, Wiley Interscience, p1216–1218. A non-limiting example of this transformation would involve the use of water as solvent, optionally in the presence of an inert organic solvent such as an ether, e.g. a cyclic ether such as tetrahydrofuran or an amide, e.g. a substituted amide such as dimethylformamide, in the presence of sodium dithionite at elevated temperature, preferably 65–80° C.

The nitro derivatives of general formula (VII) may be prepared by reaction of the pyrimidinones (VIII)

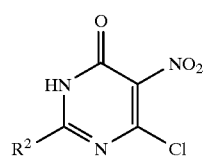

(VIII)

with amines of general formula $H_2N-(CR^4R^5)_nR^3$ (IX).

This reaction may be performed using standard conditions as envisaged by those skilled in the art. Thus, for example the reaction may be achieved in a solvent, for example an inert organic solvent such as ether, e.g. a cyclic ether such as tetrahydrofuran, an amide e.g. a substituted amide such as dimethylformamide or an alcohol such as ethanol, at a high temperature, preferably the boiling point of the solvent, in the presence of a base, e.g. an organic base such as an amine, e.g. triethylamine or a cyclic amine such as N-methylmorpholine.

The preparation of the nitro derivatives (VIII) ($R^2=NH_2$) are documented in C. Temple et al., Nucleic Acid Chemistry, Volume (I) (1978), Wiley New York, Eds L. B. Townsend et al., p47–52.

As a further extension of the invention, intermediates of formula (V) (when $R^2=NH_2$) can also be prepared from pyrimidines of formula (X)

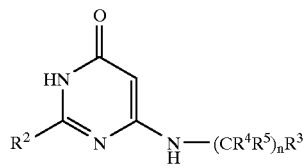

(X)

This reaction may be performed using standard conditions for amination reactions of this type. Thus, for example the reaction may be achieved in a solvent, for example water or an organic acid such as acetic acid or aqueous mixtures thereof, in the presence of sodium nitrite, at a low temperature, e.g. 0° C. to ambient temperature, such as 10° C. After work up procedures evident to those skilled in the art, the residue may be dissolved in a suitable solvent such as water, optionally in the presence of a cosolvent, for example an inert organic solvent such as an ether, e.g. a cyclic ether such as tetrahydrofuran or an amide, e.g. a substituted amide such as dimethylformamide, in the presence of a reducing agent, for example sodium dithionite, at a temperature ranging from ambient temperature to the reflux temperature of the solvent.

The pyrimidines of general formula (X) may be prepared from the intermediates of general formula (XI)

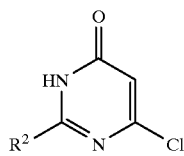

(XI)

and amines of general formula (IX), using comparable conditions to those outlined for the preparation of intermediates of general formula (VII), and conditions described in C. W. Noell et al., J. Med. Chem., 5, 558 (1962).

Amines of general formula (IX) are either commercially available or are readily accessed from commercially available compounds, using methodology known to those skilled in the art. This would include, where appropriate, homochiral starting materials for the generation of single isomer compounds of formula (I).

As a yet further extension of the present invention, compounds of formula (I) in which $R^1$ is H and $R^2$ is H or $NH_2$ can be prepared from intermediates of general formula (XII) via hydrolysis.

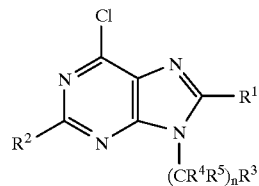

(XII)

The hydrolysis reaction may be performed using standard conditions for hydrolysis reactions of this type. Thus, for example the reaction may be carried out in a solvent, such as water, optionally in the presence of a cosolvent, for example an inert organic solvent such as an alcohol, e.g. methanol or an amide, e.g. a substituted amide such as dimethylformamide in the presence of an inorganic hydroxide containing base, e.g. sodium hydroxide, at an elevated temperature such as the boiling point of the solvent.

Intermediates of general formula (XII) may be prepared by coupling a purine of general formula (XIII)

(XIII)

with an intermediate of general formula $R^{12}(CR^4R^5)_nR^3$ (XIV) in which $R^{12}$ represents a halogen or a suitable leaving group such as an alkylsulphonate ester, e.g. methanesulphonate, or an arylsulphonate ester, e.g. 4-toluenesulphonate.

Intermediates of general formula (XIII) are either commercially available or may be made using methods evident to those skilled in the art.

The coupling reaction may be performed using standard conditions for reactions of this type. Thus, for example the reaction may be achieved in a solvent, for example an inert organic solvent such as an ether, e.g. a cyclic ether such as tetrahydrofuran, an amide e.g. a substituted amide such as dimethylformamide or an alcohol such as methanol, in the presence of a suitable base, for example an inorganic base such as potassium carbonate, or an organic base such as an amine, e.g. triethylamine, at a temperature between ambient temperature and the reflux temperature of the solvent, preferably 80° C.

Intermediates of general formula (XIV) are either commercially available or are readily accessed from commercially available compounds, using methodology known to those skilled in the art. This would include, where appropriate, homochiral starting materials for the generation of single isomer compounds of formula (I).

As a yet further extension of the present invention, compounds of formula (I) where $R^1$ and $R^2$ are the same or different and are H or NH, can be prepared from intermediates of general formula (XV) via deprotection.

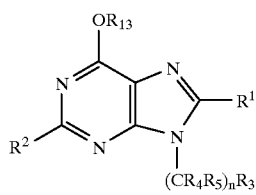

(XV)

Where $R^{33}$ represents a group such as benzyl or substituted benzyl that can be removed using standard conditions for removal of such groups. Thus, for example the reaction may be carried out in a solvent such as an alcohol, such as ethanol, optionally in the presence of an acid, for example an inorganic acid such as hydrochloric acid. In the presence of a catalyst, for example palladium on charcoal catalyst under an atmosphere of hydrogen gas at ambient temperature.

Intermediates of the general formula (XV) may be prepared by coupling a purine of general formula (XVI)

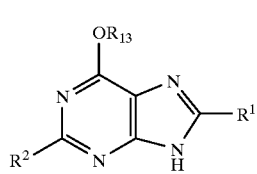

(XVI)

with an intermediate of general formula (XIV) in which $R^3$, $R^4$, $R^5$ and $R^{12}$ may be as previously described or may be in a masked form that is revealed on deprotection. An example of such a masked group would be an unsaturated alkyl moiety that could be converted to an alkyl moiety on treatment with a reducing agent such as hydrogen in the presence of a metal catalyst such as but not limited to palladium on charcoal.

The coupling reaction may be performed using standard conditions for reactions of this type. Thus, for example the reaction may be achieved in a solvent, for example an inert organic solvent such as an amide e.g. a substituted amide such as dimethylformamide in the presence of a suitable base, for example an inorganic base such as sodium hydride, at a temperature between ambient temperature and the reflux temperature of the solvent, preferably 80° C.

Intermediates of general formula (XVI) may be prepared by a modification of the procedure given by S. Ram et al Heterocycles 1978, 22 (1984) or M.-Y. Chae et al J. Med. Chem. 359, 38(2), (1995).

Compounds of formula (I) may also be prepared by interconversion of other compounds of formula (I). Thus, for example, a compound of formula (I) wherein $R^1$ is halogen (e.g. bromine) and $R^2$ is H or $NH_2$ may be prepared by halogenation (using bromine-water at ambient temperature) of a compound of formula (I) wherein $R^1$ is H and $R_2$ is H or $NH_2$. Similarly, a compound of formula (I) wherein $R^1$ is $NH_2$ may be prepared by amination (using ammonium hydroxide at 150° C.) of a compound of formula (I) wherein $R^1$ is halogen (e.g. bromine).

Advantageously those starting materials are used in said reactions that lead to the formation of those compounds indicated above as being preferred.

The invention also relates to any novel starting materials and processes for their manufacture.

Any mixtures of final products or intermediates obtained can be separated on the basis of the physico-chemical differences of the constituents, in known manner, into the pure final products or intermediates, for example by chromatography, distillation, fractional crystallization, or by formation of a salt if appropriate or possible under the circumstances.

The compounds of the invention or intermediates can also be obtained in the form of their hydrates, or include other solvents used for their crystallization.

This invention also relates to a method of treatment for patients (including man and/or mammalian animals raised in the dairy, meat or fur industries or as pets) suffering from disorders or diseases associated with purine nucleoside phosphorylase as outlined above, and more specifically, a method of treatment involving the administration of the purine nucleoside phosophorylase inhibitors of formula (I) as the active constituents.

Accordingly, the compounds of formula (I) can be used among other things in the treatment of autoimmune diseases, transplant rejection, psoriasis, gout, rheumatoid arthritis, myasthenia gravis, Type I diabetes, discoid lupus erythematosis, systemic lupus erythematosis, multiple sclerosis, T-cell cancers including but not limited to T-cell leukaemia and cutaneous T-cell lymphoma, atopic dermatitis, contact dermatitis, or other chronic allergic conditions, such as asthma, eczema, irritable bowel disease or malaria.

Additionally, the compounds of formula (I) can be used to potentiate the antiviral and antitumor effect of antiviral or antitumor purine nucleosides that may be metabolically degraded by PNP.

Hence, a further embodiment of the invention relates to a method of inhibiting the phosphorolysis and metabolic breakdown of antiviral or antitumour purine nucleosides in mammals which comprises administering in conjunction therewith to a mammal in need thereof, either separately or in combination therewith, an effective purine nucleoside phosphorylase inhibiting amount of a compound of the invention or of a said compound in combination with one or more pharmaceutically acceptable carriers. More particularly, such relates to a method of inhibiting the phosphorolysis and metabolic breakdown of purine nucleosides known in the art, e.g. of 2'-deoxyguanosine, 2',3'-dideoxyinosine, 2',3'-dideoxyguanosine or 2',3'-dideoxyadenosine.

Furthermore, the invention thus relates to a method of potentiating the antiviral or antitumor effect of a 2' or 3'-monodeoxypurine nucleosides or of 2',3'-dideoxypurine nucleosides in mammals which comprises administering in conjunction therewith to a mammal in need thereof, either separately or in combination with a said nucleoside, an effective purine nuceloside phosphorylase inhibiting amount of a compound of the invention preferably in combination with one or more pharmaceutically acceptable carriers.

More particularly, such relates to a method of enhancing or potentiating the effect of 2',3'-dideoxypurine nucleosides known in the art, e.g. 2',3'-dideoxyinosine, 2',3'-dideoxyguanosine or 2',3'-dideoxyadenosine for the treatment of retrovirus infections, e.g. HIV-retrovirus infections (acquired immunodeficiency syndrome, AIDS). 2',3'-Dideoxypurine nuceolosides are known in the art as inhibitors of HIV retrovirus infectivity and to be metabolically degraded by PNP, e.g. as described in Biochemical Pharmacology, 22, 3797 (1987). Such are administered at a pharmaceutically acceptable dose which is effective in inhibiting HIV-retrovirus infections. Preferably the lowest possible effective dose is used.

The invention further relates to pharmaceutical compositions suitable for enteral, such as oral or rectal, topical and parenteral administration, or by inhalation spray to mammals including man, which are useful to inhibit purine nucleoside phosphorylase activitiy and for the treatment of disorders responsive thereto, comprising an effective amount of a pharmacologically active compound of the invention, alone or in combination, with one or more pharmaceutically acceptable carriers. The term parenteral as used herein includes subcutaneous injections, intravenous, intrasternal injection or infusion techniques.

The pharmaceutical composition containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyeryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules where in the active ingredient is mixed with an inert solid diluent, for example calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, hydroxy-propylmethylcellulose, sodium alginate, polyvinyl-pyrrolidone, gum tragacanth and gum acacia; dispersing or wetting agents may be a naturally occuring phosphatide, for example lecithin, or condensation products of an alkylene oxide with fatty acids, for example polyoxyethylene stearate, or condensation products of ethylene oxide with long chain aliphatic alcohols,, for example heptadecaethyleneoxycetanol, or condensation products of ethylene oxide with partial esters derived from fatty acids and a hexitol such as polyoxyethylene with partial esters derived from fatty acids and hexitol anhydrides, for example polyoxyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil, or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agents and one or more preservatives. Suitable dispersing or wetting agents and suspending agents are exemplified, for example sweetening, flavouring and colouring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occuring gums, for example gum acaia or gum tragacanth, naturally-occuring phosphatides, for example soya bean, lecithin, and esters or partial esters dervied from fatty acids and hexitol anhydrides, for example sorbitan monooleate and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol and sucrose. Such formations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be in a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as folic acid find use in the preparation of injectables.

The compounds of formula (I) may also be adminstered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc. containing the compounds of formula (I) are employed. (For purposes of this application, topical application shall include mouth washes and gargles.)

Dosage levels of the order of from about 0.05 mg to about 140 mg per kilogram of body wieght per day are useful in the treatment of the above-indicated conditions (about 2.5 mg to about 7 gms per patient per day). For example, rheumatoid arthritis may be effectively treated by the administration of from about 0.01 to 50 mg of the compound per kilogram of body weight per day (about 0.5 mg to about 3.5 gms per patient per day).

The amount of active ingredient that may be combined with the carrier materials to produce a single dosage form will vary depending upon the host treated and the particular mode of administration. For example, a formulation intended for the oral administration of humans may vary from about 5 to about 95 percent of the total composition. Dosage unit forms will generally contain from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

In vitro assays for PNP were performed in 96-well plates in assay buffer containing 50 mM HEPES pH 7.4 and 1 mM potassium phosphate in a final volume of 100:1. Calf spleen PNP (0.002 units/ml) was prepared in assay buffer containing 1 mM DTT and preincubated in the presence and absence of inhibitor for 15 min at 37° C. Inhibitors were initially dissolved in DMSO and diluted with assay buffer to give a final concentration of 10%. The reaction was initiated by the addition of substrate solution consisting of a mixture of unlabelled guanosine (0.1:M) and [U-$^{14}$C]guanosine (~100,000 dpm) and incubated for 10 min at 37° C. Assays were terminated with 200:1 of activated charcoal (50 mg/ml in 8M formic acid), incubated for 10 min at room temperature, and centrifuged at 3500 rpm for 20 min. A sample of supernatant (100:1) containing free [$^{14}$C]ribose-1-phosphate was counted for 2 min by liquid scintillation counting.

Cell-based assays were carried out in 96 well plates using the human suspension cell lines MOLT-4 (T lymphocytes) and NC37 (B lymphocytes). Compounds were dissolved in DMSO and diluted in RPMI 1640 medium to give a final DMSO concentration of 0.5%. Cells were plated out in triplicate at 5×10$^4$/well (MOLT-4 and THP-1) or 2×10$^4$/well (NC37) in RPMI 1640 medium with and without 10:M 2'deoxyguanosine (dGuo) and in the presence and absence of compound. Cultures were incubated for 72 h at 37° C./5% $CO_2$ and labelled with 0.5:Ci of $^3$H-thymidine per well for the last 16 h. Cells were harvested onto filters which were counted on a scintillation counter.

The DNFB model was performed as follows: Female Balb/c mice (body weight 20 g) were sensitised by application of 25:1 of 0.5% 2,4-dinitrofluorobenzene (DNFB) to a clipped area of the abdomen on day 1. On day 6 animals were challenged by application of 0.6% DNFB to the left ear. For topical administration, compound was applied to the left ear in acetone at 30 min and again at 6 h after challenge with DNFB. For oral or i.p administration, compound was adminstered twice daily on days 1 to 6 inclusive. 24 h after challenge with DNFB, the animals were sacrificed and 6 mm punch biopsies taken from each ear and weighed.

The adjuvant arthritic rat model model used the general method described above. Briefly, male Wistar rats (body weight 180–200 g) were injected subcutaneously into the base of the tail with Freund's adjuvant (0.1 ml of a suspension of Mycobacterium Butyricum in light white oil). (Day 0 of the experiment). On day 12 the animals showing a positive response (hind paw volume increase of 20%) were allocated into groups which had statistically equivalent bodyweights and hind paw volumes. Compound was administered i.p. twice per day. Control animals were dosed with vehicle alone. Hind paw volumes were measured on days 14, 16, 18 and 22 of the experiment using a plethysmographic method. Results are expressed as the percent increase in hind paw volume compared to day 12 values. On the final day of the experiment the animals were sacrificed and X-rays taken of the hind feet (planar view). The X-rays were coded and examined in a blind fashion by two experienced independant operators and scored according to disease severity (0=normal animal, 10=severe disease including bone loss, severe erosions, significant osteophyte formation). These visual analogue scores (VAS) were averaged for three independent evaluations and both operators.

The following non-limiting Examples are intended to illustrate the preparation of compounds of formula (I), and as such are not intended to limit the invention as set forth in the claims appended, thereto.

In the Examples, the following abbreviation is used:
DCC Dicyclohexylcarbodiimide Intermediate 1

Methanesulphonyloxy-3,3-dimetliylbutane

To a stirred solution of 3,3-dimethyl-1-butanol (2 ml) in dichloromethane (48 ml), under nitrogen, was added triethylamine (4.64 ml) and the resulting solution cooled to 0/C. Methanesulphonylchloride (1.28 ml) was then added dropwise via syringe and stirring continued for 18 h as the reaction warmed to room temperature. The reaction was then concentrated onto silica and purified by flash chromatography to give the title compound as a yellow oil.
TLC (5% $CH_3OH/CH_2Cl_2$) Rf=0.15

Intermediate 2

2,8-Diamino-6-benzyloxy-9-(3',3'-dimethylbutyl) purine

To a stirred solution of 2,8-diamino-6-benzyloxypurine (Ram et al Heteocycles 1978, 22 (1984)) (0.5 g) in N,N-dimethylformamide (9 ml), under nitrogen, was added lithium hydride (95%, 20.2 mg) and stirring continued for 1 h at room temperature. Intermediate 1 (0.4 g) was then added, the resulting solution heated to 80/C and stirring continued for 18 h. The reaction was then concentrated onto silica and purified by flash chromatography to give the title compound as a beige solid.
TLC (10% $CH_3OH/CH_2Cl_2/1\%NH_3$) Rf=0.47

Intermediate 3

2,8-diamino-6-benzyloxy-9-(2'methylpropenyl) purine

Intermediate 3 was prepared in a similar manner to Intermediate 2. Thus 2,8-diamino-6-benzyloxypurine (1 g), 3-bromo-2-methylpropene (0.44 ml), LiH(40.4 mg) and dimethylformamide(15 ml) were combined to give the title compound as a yellow solid.
TLC (3% $CH_3OH/CH_2Cl_2/1\%\ NH_3$) Rf=0.32

Intermediate 4

2-Amino-6-hydroxy-4-(3'-methylbutylamino)-5-nitropyrimidine

2-Amino-4-chloro-6-hydroxy-5-nitropyrimidine (4 g), 3-methylbutylamine (1.8 g) and triethylamine (6 ml) were heated at reflux for 5 h then left stirring overnight at room temperature in ethanol. The precipitate was filtered and washed with water and air dried to yield the title compound as a yellow solid.
TLC (5% $CH_3OH/CH_2Cl_2$) Rf=0.2

Intermediate 5

2-Amino-4-(3'-methylbutylamino)-5-[1-[3-(ethoxycarbonyl)thioureido]]pyrimidin-6-[1H]-one Intermediate 4 (3.5 g) was heated to 80° C. in water (50 ml) and N,N-dimethylformamide (50 ml) while sodium dithionite (21 g) was added portionwise. After 1 h acetonitrile (100 ml) was added followed by ethoxycarbonylisothiocyanate (6 g) and the whole reaction heated at reflux for 4 h. The reaction was poured into water (1 l) and the precipitate collected by filtration. The residue was washed with water and dried in vacuo at 50°. This gave the title compound as a white powder
TLC (10% $CH_3OH/CH_2Cl_2$) Rf=0.5

Intermediate 6

Ethyl 6-amino-4-(3'-methylbutylamino)oxazolo-[5,4d]-pyrmidine-2-carbamate

Intermediate 5 (1.6 g) was stirred in N,N-dimethylformamide (30 ml) with DCC (2.9 g) under an atmosphere of dry nitrogen foe 28 h. the solvent was removed in vacuo and the residue stirred in warm toluene for 1 h. The non-soluble material was collected and washed with fresh toluene and dried in vacuo at 50° C. This gave the title compound as a buff coloured solid.
TLC (10% $CH_3OH/CH_2Cl_2$) Rf=0.4

EXAMPLE 1

8-Amino-9-(3',3'-dimethylbutyl)guanine dihydrochloride

Intermediate 2 (100 mg), ethanol (60 ml) and hydrochloric acid (1M, 3 ml) were combined and stirred in a stream of nitrogen at room temperature. 10% palladium on carbon (60 mg) was then added and the mixture stirred under an atmosphere of hydrogen for 3 d. The solution was then filtered through celite and concentrated in vacuo to give the title compound as an off white solid.
TLC (10% $CH_3OH/CH_2Cl_2/1\%NH_3$) Rf=0.0
$^1$H NMR (DMSO, 200 MHz) 0.95 (9 H,s), 1.55 (2 H,m), 3.9 (2 H,m), 6.9 (2 H,br.s), 8.2 (2 H,br.s), 11.25 (1 H,br.s)

EXAMPLE 2

8-Amino-9-(2'-methylpropyl)guanine dihydrochloride

Example 2 was prepared in a similar manner to example 1. Thus Intermediate 3 (100 mg), Pd/C (10% Pd, 60 mg), ethanol (60 ml) and hydrochloric acid (1M, 3 ml) were combined to give the title compound as an off white solid.
TLC (10% $CH_3OH/CH_2Cl_2/1\%NH_3$) Rf=0.0
$^1$H NMR (DMSO,200 MHz) 0.85 (6 H,d), 2.15 (1 H,m), 3.7 (2 H,d), 6.9 (2 H,br.s), 8.05 (2 H,br.s), 11.15 (1 H,br.s)

EXAMPLE 3

8-Amino-9-(3'-methylbutyl)guanine

Intermediate 6 (1.2 g) was stirred at reflux in methanol (30 ml) with potassium carbonate (1.6 g) for 8 h. the solvent was removed in vacuo to give a black solid. Water (30 ml) was added and the black reaction mixture heated at reflux for 14 h. the resultant solid was filtered and washed with water to give the title compound as a pale yellow solid.
TLC (10% $CH_3OH/CH_2Cl_2$) Rf=0.1
$^1$H NMR (DMSO, 200 MHz) 0.95 (6 H,d), 1.5 (3 H,m), 3.8 (2 H,m), 6.0 (2 H,br.s), 6.35 (2 H,br.s), 10.9 (1 H,br.s)

EXAMPLE 4

8-Amino-9-(3'-methylbutyl)guanine dihydrochloride

Example 3 (0.2 g) was cooled in an ice bath in dry methanol (15 ml) under a nitrogen atmosphere and acetyl chloride (0.2 ml) was added. after 0.25 h stirring at room temperature the solvent was removed and the solid obtained recrystallised from ethyl acetate with 10% methanol. The title compound was obtained as a pale yellow solid.
TLC (10% $CH_3OH/CH_2Cl_2/1\%NH_3$) Rf=0.0
$^1$H NMR (DMSO 200 MHz) 0.95 (6 H,d), 1.6 (3 H,m), 3.95 (2 H,br.t), 7.2 (2 H,br.s), 8.4 (2 H,br.s), 11.5 (1 H,br.s)

We claim:

1. A compound of formula (I):

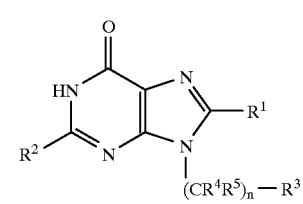

(I)

wherein
n=1 or 2;
$R^1$ is $NH_2$;
$R^2$ is H or $NH_2$;
$R^3$ represents the group $CR^6R^7R^8$ where $R^6$, $R^7$ and $R^8$ are the same or different and are each H, $C_{1-6}$ alkyl or $C_{1-6}$ haloalkyl;
$R^4$ and $R^5$ are the same or different and are selected from the group consisting of H, $CO_2H$, $CO_2C_{1-6}$, $NHSO_2CF_3$, tetrazole and $(CR^9R^{10})_p(Y)_q(CR^9R^{10})_tZ$;
$R^9$ and $R^{10}$ are the same or different and are each $C_{0-6}$ alkyl-Z;
p=1–3;
q=0 or 1;
t=0–4, provided that t>0 when q=1;
Y=O, NH or $S(O)_m$ where m=0–2; and
Z is selected from a group consisting of H, CN, $CO_2H$, $CO_2C_{1-6}$ alkyl, $NHSO_2CF_3$ tetrazole, triazole, $CONH_2$, $CON(C_{1-6}$ alkyl$)_2$, $CONH(C_{1-6}$ alkyl), SO, N H $(C_{1-6}$ alkyl) and $SO_2N(C_{1-6}$ alkyl$)_2$;
or a salt, solvate or hydrate thereof.

2. The compound of claim 1, selected from the group consisting of
8-Amino-9-(3',3'-dimethylbutyl)guanine,
8-Amino-9-(2'-methylpropyl)guanine, and
8-Amino-9-(3'-methylbutyl)guanine,
and salts thereof.

3. The compound of claim 1 in the form of a single enantiomer or diastereoisomer.

4. A pharmaceutical composition, comprising a compound of claim 1, and a pharmaceutically acceptable diluent, or carrier.

5. A method for treating a human or animal having a condition that can be treated by the inhibition of purine nucleoside phosphorylase, said method comprising treating said human or animal with an effective amount of a compound of claim 1, or a salt, solvate, or hydrate thereof, wherein said condition is selected from the group consisting of gout, rheumatoidarthritis, and psoriasis.

6. The method according to claim 5, wherein said compound is selected from the group consisting of 8-Amino-9-(3',3'-dimethylbutyl)guanine, 8-Amino-9-(2'-methylpropyl)guanine, and 8-Amino-9-(3'-methylbutyl)guanine, and salts thereof.

7. The method according to claim 5, wherein said compound is in association with a pharmaceutically acceptable diluent or carrier.

\* \* \* \* \*

UNITED STATES PATENT AND TRADEMARK OFFICE
CERTIFICATE OF CORRECTION

PATENT NO.    : 5,912,252

DATED         : June 15, 1999

INVENTOR(S)   : Steven Colin Beasley, John Gary Montana

It is certified that error appears in the above-identified patent and that said Letters Patent is hereby corrected as shown below:

Column 18, line 43: "$CO_2C_{1-6}$," should read --$CO_2C_{1-6}$ alkyl,--.

Column 18, line 54: "SO," should read --$SO_2$--.

Column 19, line 7: "rheumatoidarthritis," should read --rheumatoid arthritis--.

Signed and Sealed this

Fifteenth Day of February, 2000

*Attest:*

Q. TODD DICKINSON

*Attesting Officer*    *Commissioner of Patents and Trademarks*